(12) United States Patent
Oonuki et al.

(10) Patent No.: US 8,870,775 B2
(45) Date of Patent: Oct. 28, 2014

(54) ULTRASONIC DIAGNOSTIC APPARATUS AND ULTRASONIC DIAGNOSTIC PROCESSING METHOD

(75) Inventors: Yutaka Oonuki, Otawara (JP);
Hiroyuki Shikata, Nasushiobara (JP);
Hideki Kosaku, Nasushiobara (JP);
Takashi Ogawa, Nasushiobara (JP);
Minoru Aoki, Nasushiobara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 884 days.

(21) Appl. No.: 11/680,949

(22) Filed: Mar. 1, 2007

(65) Prior Publication Data

US 2007/0239021 A1    Oct. 11, 2007

(30) Foreign Application Priority Data

Mar. 2, 2006    (JP) ................ 2006-056464

(51) Int. Cl.
*A61B 8/12*    (2006.01)
*A61B 8/00*    (2006.01)
*G01S 7/52*    (2006.01)
*G01S 15/89*    (2006.01)
*A61B 8/08*    (2006.01)

(52) U.S. Cl.
CPC .............. *A61B 8/4461* (2013.01); *A61B 8/4488* (2013.01); *A61B 8/465* (2013.01); *A61B 8/12* (2013.01); *A61B 8/463* (2013.01); *G01S 7/52074* (2013.01); *G01S 15/894* (2013.01); *A61B 8/483* (2013.01); *A61B 8/4483* (2013.01)
USPC ......................................... 600/443; 600/462

(58) Field of Classification Search
USPC ................................... 600/462, 443
See application file for complete search history.

(56) References Cited

U.S. PATENT DOCUMENTS

| 4,543,960 | A |   | 10/1985 | Harui et al. |
|---|---|---|---|---|
| 4,756,313 | A | * | 7/1988 | Terwilliger .............. 600/462 |
| 5,181,514 | A | * | 1/1993 | Solomon et al. ........... 600/444 |
| 5,207,225 | A |   | 5/1993 | Oaks et al. |
| 5,402,793 | A |   | 4/1995 | Gruner et al. |
| 8,315,720 | B2 | * | 11/2012 | Mohr et al. ............... 700/83 |
| 2005/0277836 | A1 |   | 12/2005 | Proulx et al. |
| 2007/0021738 | A1 | * | 1/2007 | Hasser et al. ............. 606/1 |

FOREIGN PATENT DOCUMENTS

| EP | 0 514 584 A2 | 11/1992 |
|---|---|---|
| EP | 0 984 298 A2 | 3/2000 |
| JP | 5-51313 | 7/1993 |

(Continued)

OTHER PUBLICATIONS

Japanese Office Action issued May 17, 2011, in Patent Application No. 2006-056464 (with English-language translation).

*Primary Examiner* — Long V. Le
*Assistant Examiner* — Angela M Hoffa
(74) *Attorney, Agent, or Firm* — Oblon, Spivak, McClelland, Maier & Neustadt, L.L.P.

(57) ABSTRACT

A generating unit generates a plurality of ultrasonic cross-sectional images at a plurality of angles when an ultrasonic wave emitting surface in an ultrasonic probe is rotated. A regenerating unit saves information on the angle of the ultrasonic wave emitting surface when a predetermined condition is satisfied, and rotates the ultrasonic wave emitting surface from the angle of the ultrasonic wave emitting surface different from the saved angle information to the angle based on the saved angle information.

16 Claims, 3 Drawing Sheets

(56) References Cited

FOREIGN PATENT DOCUMENTS

| JP | 10-314166 | 12/1998 |
| JP | 2000-79121 | 3/2000 |
| JP | 2000-139924 | 5/2000 |
| JP | 2000-325345 | 11/2000 |
| JP | 2003-334198 | 11/2003 |

* cited by examiner

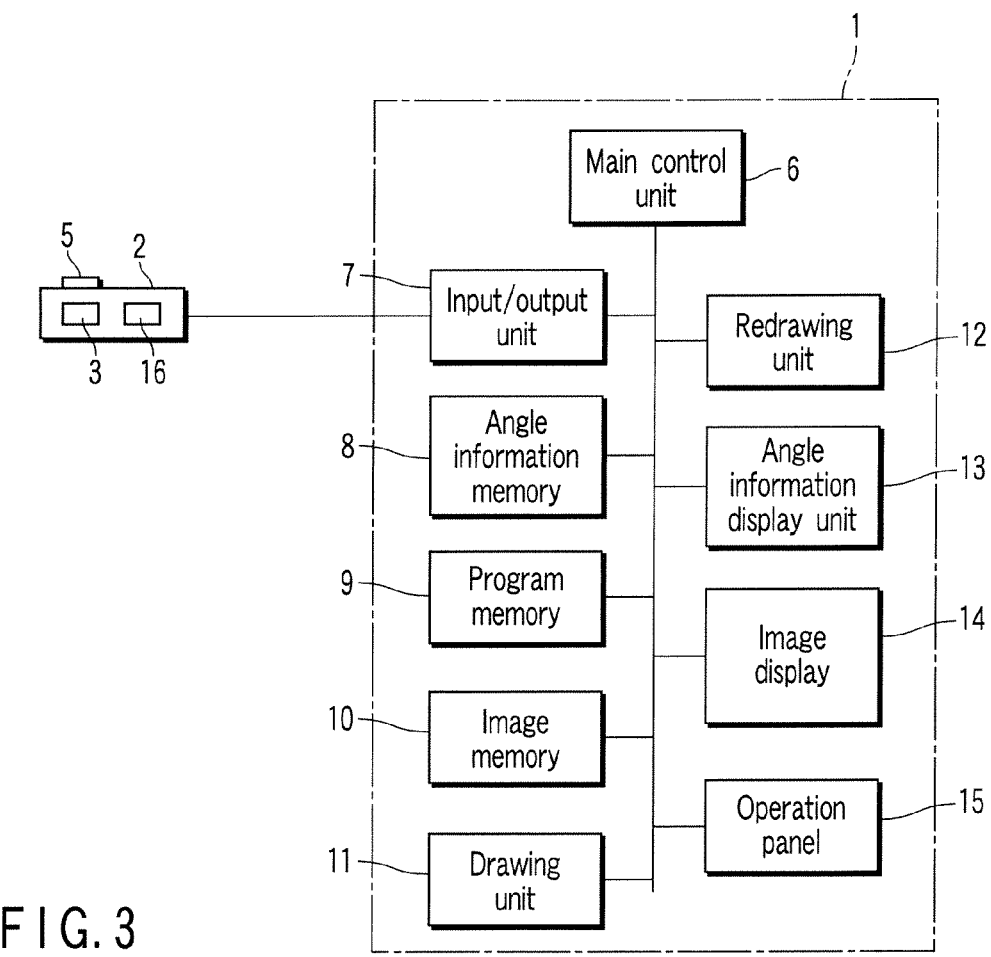
F I G. 3
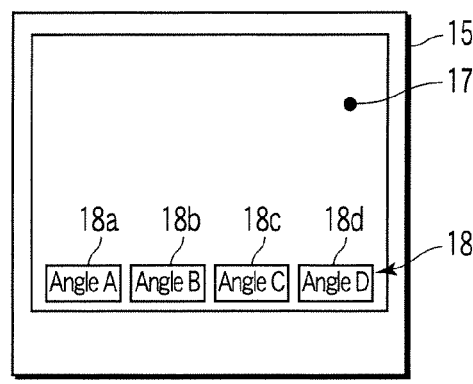
F I G. 4
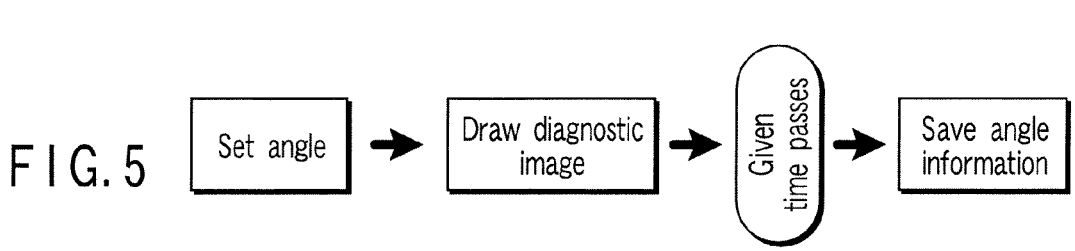
F I G. 5

ULTRASONIC DIAGNOSTIC APPARATUS AND ULTRASONIC DIAGNOSTIC PROCESSING METHOD

CROSS-REFERENCE TO RELATED APPLICATIONS

This application is based upon and claims the benefit of priority from prior Japanese Patent Application No. 2006-056464, filed Mar. 2, 2006, the entire contents of which are incorporated herein by reference.

BACKGROUND OF THE INVENTION

1. Field of the Invention

The present invention relates to an ultrasonic diagnostic apparatus and an ultrasonic diagnostic processing method in which a surface emitting ultrasonic waves emitted from an ultrasonic probe is rotated on an axis of this ultrasonic wave emitting surface and this rotation is used to generate a plurality of ultrasonic cross-sectional images from a plurality of angles to a subject.

2. Description of the Related Art

An ultrasonic diagnostic apparatus scans the inside of a specimen with ultrasonic waves generated from an ultrasonic probe, and receives reflected waves from the inside of the specimen. The ultrasonic diagnostic apparatus acquires an ultrasonic diagnostic image of the inside of the specimen on the basis of a reception signal generated from the reflected waves from the inside of the specimen. In a diagnosis using the ultrasonic diagnostic apparatus, when a specimen such as one human body is inspected, a plurality of ultrasonic diagnostic images of the inside of the specimen may be generated. In this case, the ultrasonic diagnostic images may be saved.

Some of the ultrasonic diagnostic apparatuses conduct a transesophageal ultrasonic diagnosis. A transesophageal ultrasonic diagnostic apparatus comprises an ultrasonic probe. The ultrasonic probe allows the rotation of an ultrasonic wave emitting surface on the direction of this ultrasonic wave emitting surface. That is, the ultrasonic probe comprises a mechanism for rotating the ultrasonic wave emitting surface. For example, as shown in FIG. 10, the transesophageal ultrasonic diagnostic apparatus sets the angle of the ultrasonic wave emitting surface in the ultrasonic probe, generates an ultrasonic diagnostic image at the set angle, and then saves the generated ultrasonic diagnostic image.

In a diagnosis using the transesophageal ultrasonic diagnostic apparatus, a plurality of ultrasonic diagnostic images may be sequentially generated from a plurality of angular directions to a certain region of the inside of a specimen during the inspection of the specimen. In a series of operations for sequentially generating the ultrasonic diagnostic images from the plurality of angular directions, the ultrasonic diagnostic images may be generated in the following manner. First, an ultrasonic diagnostic image is saved at an arbitrary angle. Then, an ultrasonic diagnostic image is generated at an angle different from the arbitrary angle. Subsequently, an ultrasonic diagnostic image is again generated returning to the arbitrary angle.

The ultrasonic diagnostic image again generated corresponds to a region of the specimen which is important, for example, in diagnosing the specimen and which requires another observation. When an ultrasonic diagnostic image at the arbitrary angle is again generated, a rotating knob or switch provided in the ultrasonic probe is operated. Thus, the angle in the direction of the ultrasonic wave emitting surface is adjusted, and the ultrasonic diagnostic image at the arbitrary angle is generated.

Some of the ultrasonic diagnostic apparatuses comprise a mechanism which mechanically swings the ultrasonic probe in a slicing direction. In a diagnosis using such an ultrasonic diagnostic apparatus, an observation and a diagnosis are conducted concerning ultrasonic diagnostic images from a plurality of angular directions to, for example, a target within the specimen. In the above observation and diagnosis, an ultrasonic diagnostic image is observed and diagnosed at an arbitrary angle. Then, an ultrasonic diagnostic image is observed and diagnosed at an angle different from the arbitrary angle. Again, an ultrasonic diagnostic image at the arbitrary angle is observed and diagnosed. In this case, the operation of again generating the ultrasonic diagnostic image at the arbitrary angle is carried out looking at the ultrasonic diagnostic images.

An angle at which the ultrasonic diagnostic image is generated in a rotated direction of the ultrasonic wave emitting surface is saved as angle information. The angle information for the ultrasonic diagnostic image is added to the ultrasonic diagnostic image and saved together when this ultrasonic diagnostic image is saved. Then, the angle information is generally displayed together with the display of the ultrasonic diagnostic image.

According to the disclosure of Jpn. Pat. Appln. KOKAI Publication No. 2000-79121, when the updating of the display of the images is temporarily stopped in accordance with an instruction from an operator during a cine-display in which a plurality of images stored in a memory are sequentially displayed in a time-series order, the image displayed when the updating is stopped is automatically saved, and the automatically saved image is displayed in accordance with a call operation from the operator.

Therefore, when the ultrasonic diagnostic images at a plurality of angles are sequentially generated and the ultrasonic diagnostic image at the angle at which the diagnosis has been completed is again generated, it is necessary to operate the rotating knob or switch provided in the ultrasonic probe and carry out the regenerating looking at the ultrasonic diagnostic images. Thus, the operation once performed has to be performed again for the regenerating of the ultrasonic diagnostic image. This leads to an increase in diagnostic time.

In is an object of the present invention to provide an ultrasonic diagnostic apparatus and an ultrasonic diagnostic processing method which enable the regenerating of an ultrasonic diagnostic image at a desired angle with a simple operation to achieve a reduction in inspection time.

BRIEF SUMMARY OF THE INVENTION

An ultrasonic diagnostic apparatus according to a first aspect of the present invention comprises: an ultrasonic probe in which a surface emitting ultrasonic waves is rotatable on an axis in the direction of this ultrasonic wave emitting surface; a generating unit which generates a plurality of ultrasonic cross-sectional images at a plurality of angles when the ultrasonic wave emitting surface in the ultrasonic probe is rotated; and a regenerating unit which saves information on the angle of the ultrasonic wave emitting surface when a predetermined condition is satisfied and which rotates the ultrasonic wave emitting surface from the angle of the ultrasonic wave emitting surface different from the saved angle information to the angle based on the saved angle information.

An ultrasonic diagnostic processing method according to a second aspect of the present invention comprises: rotating a surface emitting ultrasonic waves emitted from an ultrasonic probe on the direction of this ultrasonic wave emitting surface; generating a plurality of ultrasonic cross-sectional images at a plurality of angles when the ultrasonic wave emitting surface in the ultrasonic probe is rotated; saving information on the angle of the ultrasonic wave emitting surface when a predetermined condition is satisfied; and rotating the ultrasonic wave emitting surface from the angle of the ultrasonic wave emitting surface different from the saved angle information to the angle based on the saved angle information.

BRIEF DESCRIPTION OF THE SEVERAL VIEWS OF THE DRAWING

FIG. 3 is a block configuration diagram showing a diagnostic processing device in the same apparatus;

FIG. 4 is a diagram showing one example of angle information displayed on a display screen of an operation panel in the same apparatus;

FIG. 5 is a diagram showing the flow of a method of saving the angle information for an ultrasonic diagnostic image in the same apparatus;

DETAILED DESCRIPTION OF THE INVENTION

Figure 1:
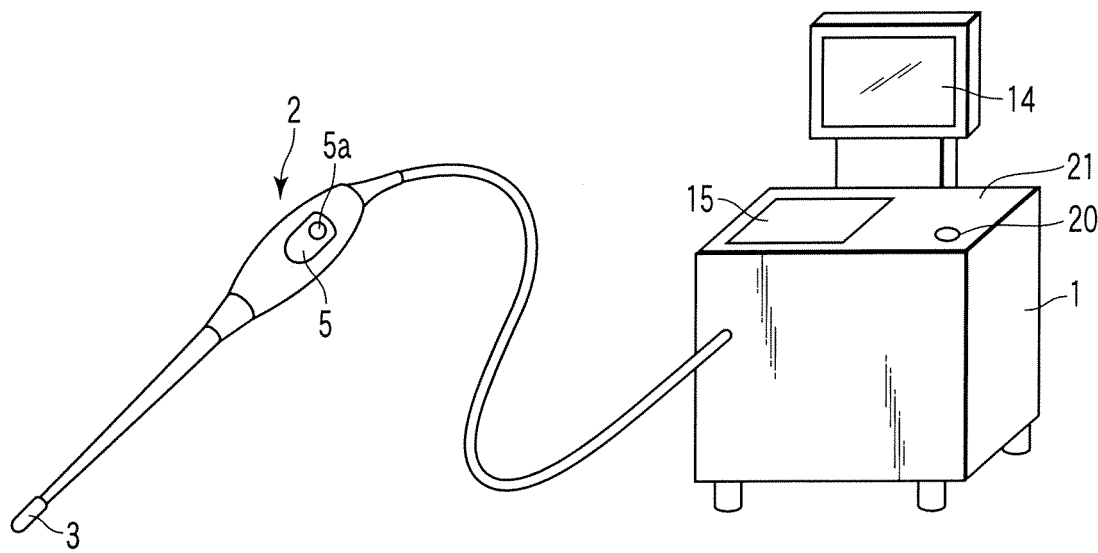
FIG. 1 is an external configuration diagram showing a first embodiment of an ultrasonic diagnostic apparatus according to the present invention.

Hereinafter, a first embodiment of the present invention will be described with reference to the drawing.

Figure 2:
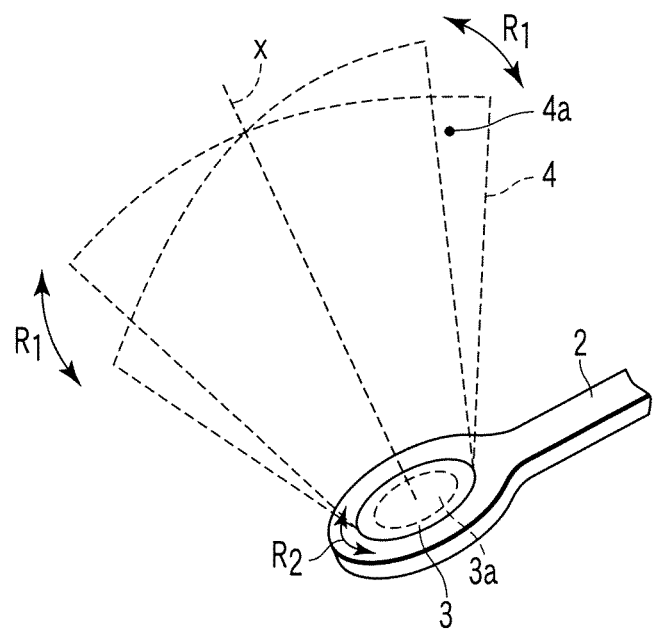
FIG. 2 is a schematic diagram showing the rotation of a surface emitting ultrasonic waves transmitted from the distal end of an ultrasonic probe in the same apparatus.

FIG. 1 shows a diagram of the external appearance of an ultrasonic diagnostic apparatus applied to a transesophageal ultrasonic diagnosis. A ultrasonic probe 2 is connected to an ultrasonic diagnostic apparatus 1. As shown in FIG. 2, a plurality of ultrasonic wave oscillating elements 3 are provided at the distal end of the ultrasonic probe 2. Each of the ultrasonic wave oscillating elements 3 transmits ultrasonic waves 4.

The ultrasonic wave oscillating elements 3 are, for example, one-dimensionally arranged. An acoustic lens 3a is provided in front of the ultrasonic wave oscillating elements 3. The acoustic lens 3a converges the ultrasonic waves 4 emitted from each of the ultrasonic wave oscillating elements 3. Each of the one-dimensionally arranged ultrasonic wave oscillating elements 3 can mechanically rotate, for example, in a direction of an arrow $R_2$. When each of the ultrasonic wave oscillating elements 3 mechanically rotates in the direction of the arrow $R_2$, an ultrasonic wave emitting surface 4a rotates in a direction of an arrow $R_1$.

Alternatively, the ultrasonic wave oscillating elements 3 are arranged, for example, on a two-dimensional plane. The ultrasonic wave oscillating elements 3 arranged on the two-dimensional plane are electrically driven/controlled so that some of the ultrasonic wave oscillating elements 3 emit the ultrasonic waves 4 and some of the ultrasonic wave oscillating elements 3 do not emit the ultrasonic waves. Thus, each of the ultrasonic wave oscillating elements 3 rotates, in the direction of the arrow $R_1$, the ultrasonic wave emitting surface 4a for the ultrasonic waves 4 to be emitted.

Each of the one-dimensionally or two-dimensionally arranged ultrasonic wave oscillating elements 3 rotates, in the direction of the arrow $R_1$, the ultrasonic wave emitting surface 4a on an axis x included in the direction of the surface emitting the ultrasonic waves 4. An axis x is set within the ultrasonic wave emitting surface 4a of the ultrasonic waves 4. The axis x is set to be, for example, in the center of the ultrasonic wave oscillating elements 3, and to be vertical to the one-dimensional direction or two-dimensional plane in which the ultrasonic wave oscillating elements 3 are arranged.

An operation portion 5 is provided in a grip of the ultrasonic probe 2. The operation portion 5 is provided with, for example, various switches for operating the ultrasonic probe 2. The operation portion 5 is provided with a switch 5a for regenerating.

FIG. 3 is a block configuration diagram of the ultrasonic diagnostic apparatus 1. The ultrasonic diagnostic apparatus 1 computer-processes an output signal of the ultrasonic probe 2 to obtain an ultrasonic cross-sectional image of a specimen. The ultrasonic diagnostic apparatus 1 has a main control unit 6 configured by, for example, a CPU. To the main control unit 6, there are connected an input/output unit 7, an angle information memory 8, a program memory 9, an image memory 10, a generating unit 11, a regenerating unit 12, an angle information display unit 13, an image display 14 and an operation panel 15. In addition, regarding the regenerating unit 12 and the angle information display unit 13 in FIG. 3, functions when a program for ultrasonic diagnostic processing is processed by a computer are shown in block diagrams.

The main control unit 6 executes the program for the ultrasonic diagnostic processing stored in the program memory 9 in order to save data in or read data from the angle information memory 8 and the image memory 10, to send operation commands to the input/output unit 7, the regenerating unit 12 and the angle information display unit 13, to display images on the image display 14, and to receive the operation commands from the operation panel 15.

The ultrasonic probe 2 is connected to the input/output unit 7. The ultrasonic probe 2 is provided with an angle sensor 16. The angle sensor 16 detects the mechanical angle of each of the ultrasonic wave oscillating elements 3 which are, for example, one-dimensionally arranged. For example, the angle sensor 16 detects the angle of rotation in, for example, a slicing direction of each of the one-dimensionally arranged ultrasonic wave oscillating elements 3, and outputs an angle signal corresponding to this angle. Further, the angle sensor 16 detects the angle of the ultrasonic wave emitting surface 4a of the ultrasonic waves 4 emitted from each of the ultrasonic wave oscillating elements 3 which are, for example, two-dimensionally arranged. In the case of the two-dimensionally arranged ultrasonic wave oscillating elements 3, the angle sensor 16 detects the angle of the ultrasonic wave emitting surface 4a of the ultrasonic waves 4 rotated in the direction of the arrow $R_1$, for example, in accordance with the driving/control of each of the ultrasonic wave oscillating elements 3, and outputs an angle signal corresponding to the detected angle.

Whether the ultrasonic wave oscillating elements 3 are arranged one-dimensionally or two-dimensionally, the angle sensor 16 detects the angle in the direction of the arrow $R_1$ of the ultrasonic wave emitting surface 4a of the ultrasonic waves 4 emitted from each of the ultrasonic wave oscillating elements 3. The angle of the ultrasonic wave emitting surface 4a of the ultrasonic waves 4 is, for example, an angle to a preset referential angle position.

The angle information memory 8 stores as angle information the angle signal output from the angle sensor 16.

The program memory 9 stores the program for the ultrasonic diagnostic processing executed by the CPU of the computer. The program for the ultrasonic diagnostic processing causes the ultrasonic cross-sectional images from a plurality of angles to be generated on the image display 14 when the ultrasonic wave emitting surface 4a of the ultrasonic probe 2 is rotated on the axis x. The program for the ultrasonic diagnostic processing causes the information on the angle of the ultrasonic wave emitting surface 4a to be saved in the angle information memory 8 when a predetermined condition is satisfied, and causes the ultrasonic wave emitting surface 4a to be rotated from the angle of the ultrasonic wave emitting surface 4a different from the saved angle information to an angle based on the angle information saved in the angle information memory 8. The program for the ultrasonic diagnostic processing includes a program for saving the angle information in the angle information memory 8 when the angle at which the ultrasonic cross-sectional image is generated is maintained for a given time.

When the ultrasonic wave emitting surface 4a of the ultrasonic probe 2 is rotated on the axis x, the generating unit 11 generates ultrasonic cross-sectional images from a plurality of angles, and generates the ultrasonic cross-sectional images on the image display 14.

The regenerating unit 12 judges, for example, whether the angle at which the predetermined condition is satisfied, for example, at which the ultrasonic cross-sectional image is generated on the image display 14 is maintained for a given time. Specifically, the regenerating unit 12 judges whether the angle of the ultrasonic wave emitting surface 4a at which an ultrasonic cross-sectional image of a certain region within the specimen is generated remains unchanged for a preset given time. When the result of the judgment is that the angle is maintained for a given time, the regenerating unit 12 saves the angle of the ultrasonic wave emitting surface 4a at which the ultrasonic cross-sectional image is generated as angle information in the angle information memory 8. Regarding the angle information, the angle signal output from the angle sensor 16 is stored as the angle information in the angle information memory 8.

The regenerating unit 12 judges whether the switch 5a for regenerating provided in the operation portion 5 is operated. If the switch 5a for regenerating is operated, the regenerating unit 12 reads the angle information saved in the angle information memory 8. In accordance with the read angle information, the regenerating unit 12 rotates the ultrasonic wave emitting surface 4a of the ultrasonic waves 4 emitted from the ultrasonic probe 2 in the direction of the arrow $R_1$ shown in FIG. 2. Then, the regenerating unit 12 sets the angle of the ultrasonic wave emitting surface 4a of the ultrasonic waves 4 to the angle information read from the angle information memory 8. The regenerating unit 12 redraws a particular ultrasonic cross-sectional image corresponding to the angle information on the image display 14.

The regenerating unit 12 judges whether there is a touch operation for angle information 18 displayed on a display screen 17 of the operation panel 15, for example, as shown in FIG. 4. When a touch operation for the angle information 18 is performed, the regenerating unit 12 receives coordinates corresponding to the angle information 18 sent from the operation panel 15, and rotates the ultrasonic wave emitting surface 4a of the ultrasonic probe 2 in the direction of the arrow $R_1$ shown in FIG. 2 in accordance with the angle information 18 corresponding to the coordinates. Then, the regenerating unit 12 sets the angle of the ultrasonic wave emitting surface 4a of the ultrasonic waves 4 to the angle information read from the angle information memory 8, in the same manner as described above. The regenerating unit 12 redraws a particular ultrasonic cross-sectional image corresponding to the angle information on the image display 14.

The angle information display unit 13 displays the angle information saved in the angle information memory 8 on the display screen 17 of the operation panel 15. FIG. 4 shows one example of the angle information 18 displayed on the display screen 17 of the operation panel 15. The angle information 18 indicates, for example, four angles A to D. The display form of the angle information 18 for the angles A to D is not limited to the rectangular form shown in FIG. 4, and the angle information 18 may be displayed in a desired shape, display color, layout, etc. The angle information 18 indicates, for example, touch buttons 18a to 18d for the angles A to D. Coordinates to be displayed on the display screen 17 are set in the touch buttons 18a to 18d.

The operation panel 15 is formed by, for example, a touch command screen (TCS). Therefore, when one indication of the angle information 18 displayed on the display screen 17 of the operation panel 15 is touched, the operation panel 15 reads, for example, the coordinates on the display screen 17 corresponding to the touched indication of the angle information 18, and sends the coordinates corresponding to this indication of the angle information 18 to the regenerating unit 12.

Next, the operation of the redrawing in the apparatus configured as described above will be described.

The ultrasonic probe 2 scans the inside of the specimen with the ultrasonic waves 4, and receives reflected waves from the inside of the specimen. The ultrasonic probe 2 outputs a reception signal generated from the reflected waves from the inside of the specimen. The reception signal from the ultrasonic probe 2 is input to the generating unit 11 through the input/output unit 7, and the generating unit 11 acquires an ultrasonic diagnostic image of the inside of the specimen, and then displays the ultrasonic diagnostic image on the image display 14.

In a diagnosis using the transesophageal ultrasonic diagnostic apparatus, the ultrasonic wave emitting surface 4a is rotated in the direction of the arrow $R_1$ on the axis x set in the direction of the ultrasonic wave emitting surface 4a as shown in FIG. 2, during the diagnosis of the specimen. Thus, a plurality of ultrasonic diagnostic images from a plurality of angles to a certain region within the specimen are sequentially generated on the image display 14.

During the diagnosis of a certain region within the specimen, the regenerating unit 12 judges whether the angle of the ultrasonic diagnostic image of a certain region within the specimen generated on the image display 14 remains unchanged for a preset given time, for example, as shown in FIG. 5.

The fact that the angle of the ultrasonic diagnostic image remains unchanged for a preset given time means that the region in which the ultrasonic diagnostic image is generated is important in diagnosing the specimen and that this angle is the angle at which the observation of the region is needed.

Therefore, when the angle at which the ultrasonic diagnostic image is generated remains unchanged for a preset given time, the regenerating unit 12 saves, in the angle information memory 8, the angle of the ultrasonic wave emitting surface 4a at which the ultrasonic diagnostic image is generated on the image display 14, for example, the angle information for an angle A of the ultrasonic wave emitting surface 4a of the ultrasonic probe 2. The angle information display unit 13 displays the angle information saved in the angle information memory 8 as the angle information 18 on the display screen 17 of the operation panel 15, for example, as shown in FIG. 4. The angle information 18 is indicated, for example, by the touch button 18a for the angle A.

When a plurality of ultrasonic diagnostic images from a plurality of angular directions to a certain region within the specimen are sequentially generated on the image display 14 in the same manner as described above, there may be a plurality of ultrasonic diagnostic images in which the angle of the ultrasonic wave emitting surface 4a at which these ultrasonic diagnostic images are generated remains unchanged for a preset given time. In this case, the regenerating unit 12 sequentially saves the information on the angle of the ultrasonic wave emitting surface 4a of the ultrasonic probe 2 in the angle information memory 8 every time the angle of the ultrasonic wave emitting surface 4a remains unchanged for a given time.

The angle information display unit 13 displays a plurality of pieces of angle information saved in the angle information memory 8 as the angle information 18 on the display screen 17 of the operation panel 15, for example, as shown in FIG. 4. The angle information 18 is composed of, for example, the touch buttons 18a to 18d for the four angles A to D.

For example, the generating unit 11 draws an ultrasonic diagnostic image at the angle A of the ultrasonic wave emitting surface 4a of the ultrasonic probe 2. If the angle A of the ultrasonic wave emitting surface 4a remains unchanged for a given time, the regenerating unit 12 saves the angle A of the ultrasonic wave emitting surface 4a of the ultrasonic probe 2 as the angle information in the angle information memory 8. The angle A of the ultrasonic wave emitting surface 4a at this point corresponds to the touch button 18a.

Next, the generating unit 11 draws the ultrasonic cross-sectional image at the angle B of the ultrasonic wave emitting surface 4a of the ultrasonic probe 2. If the angle B of the ultrasonic wave emitting surface 4a remains unchanged for a given time, the regenerating unit 12 saves the angle B of the ultrasonic wave emitting surface 4a of the ultrasonic probe 2 as the angle information in the angle information memory 8. The angle B of the ultrasonic wave emitting surface 4a at this point corresponds to the touch button 18b.

Subsequently, the regenerating unit 12 saves the angle C of the ultrasonic wave emitting surface 4a of the ultrasonic probe 2 as the angle information in the angle information memory 8 in a similar manner. The angle C of the ultrasonic wave emitting surface 4a at this point corresponds to the touch button 18c. The regenerating unit 12 saves the angle D of the ultrasonic wave emitting surface 4a of the ultrasonic probe 2 as the angle information in the angle information memory 8. The angle D of the ultrasonic wave emitting surface 4a at this point corresponds to the touch button 18c.

Then, the ultrasonic cross-sectional image of the region may be again diagnosed at the angle of the direction of the emitting surface corresponding to the angle information 18 for the angle A displayed on the display screen 17 of the operation panel 15. In this case, the touch button 18a for the angle A is touched out of the angle information 18 displayed on the display screen 17 of the operation panel 15. The operation panel 15 reads, for example, the coordinates on the display screen 17 corresponding to the angle information 18 for the touched touch button 18a, and sends the coordinates corresponding to the angle information 18 to the regenerating unit 12.

The regenerating unit 12 receives the coordinates sent from the operation panel 15, and recognizes the angle A in the direction of the emitting surface corresponding to the touch button 18a on the basis of the coordinates. The regenerating unit 12 sends a command of the angle A to the ultrasonic probe 2. The ultrasonic probe 2 rotates the direction of the emitting surface for the ultrasonic waves 4 on the axis x in the direction of the arrow $R_1$, and sets the emitting surface at the angle A. Thus, the ultrasonic probe 2 scans the inside of the specimen with the ultrasonic waves 4 at the angle A, receives reflected waves from the inside of the specimen, and outputs a reception signal generated from the reflected waves. The reception signal from the ultrasonic probe 2 is input to the generating unit 11 through the input/output unit 7, and the generating unit 11 acquires an ultrasonic diagnostic image at the angle A, and then redraws the ultrasonic diagnostic image on the image display 14. As a result, the ultrasonic diagnostic images at the angle A which is important in diagnosing the specimen can be again diagnosed.

The ultrasonic cross-sectional images of the region may be again diagnosed at the angles in the direction of the emitting surface corresponding to the angle information 18 for the angles A and B displayed on the display screen 17 of the operation panel 15. In this case, the touch button 18a for the angle A is first touched out of the angle information 18 displayed on the display screen 17 of the operation panel 15. The operation panel 15 reads, for example, the coordinates on the display screen 17 corresponding to the angle information 18 for the touched touch button 18a, and sends the coordinates corresponding to the angle information 18 to the regenerating unit 12. The regenerating unit 12 receives the coordinates sent from the operation panel 15, and, in the same manner as described above, acquires an ultrasonic diagnostic image at the angle A, and then redraws the ultrasonic diagnostic image on the image display 14.

Next, the touch button 18b for the angle B is touched out of the angle information 18 displayed on the display screen 17 of the operation panel 15. The operation panel 15 reads, for example, the coordinates on the display screen 17 corresponding to the angle information 18 for the touched touch button 18b, and sends the coordinates corresponding to the angle information 18 to the regenerating unit 12. The regenerating unit 12 receives the coordinates sent from the operation panel 15, and, in the same manner as described above, acquires an ultrasonic diagnostic image at the angle B, and then redraws the ultrasonic diagnostic image on the image display 14.

As a result, the ultrasonic cross-sectional images, for example, when the ultrasonic wave emitting surface 4a for the ultrasonic waves 4 is at the angles A and B can be regenerated on the image display 14. The ultrasonic diagnostic images at the angles A and B which are important in diagnosing the specimen can be again diagnosed.

On the other hand, in the same manner as described above, when the specimen is diagnosed, there is an angle of the ultrasonic wave emitting surface 4a in a certain region which is important in diagnosing the specimen and which requires another observation. For example, there is a case where the ultrasonic diagnostic image which has been generated is regenerated, for example, at one angle before the angle of the ultrasonic wave emitting surface 4a at which the ultrasonic diagnostic image is currently being generated on the image display 14. In this case, the switch 5a for redrawing provided in the operation portion 5 is operated.

In response to the operation of the switch 5a for redrawing, the regenerating unit 12 reads, from the angle information memory 8, the previous angle information, for example, reads the angle such as the angle A which is one angle before the angle at which the ultrasonic diagnostic image is currently generated. The regenerating unit 12 redraws, on the image display 14, the ultrasonic diagnostic image at the angle in the direction of the emitting surface corresponding to the angle information for the angle A.

In this case, the regenerating unit 12 sends a command of the angle A to the ultrasonic probe 2. The ultrasonic probe 2 rotates the ultrasonic wave emitting surface 4a for the ultrasonic waves 4 on the axis x in the direction of the arrow $R_1$, and sets the ultrasonic wave emitting surface 4a at the angle A. Thus, the ultrasonic probe 2 scans the inside of the specimen with the ultrasonic waves 4 at the angle A. The ultrasonic probe 2 receives reflected waves from the inside of the specimen, and outputs a reception signal generated from the reflected waves. The reception signal from the ultrasonic probe 2 is input to the generating unit 11 through the input/output unit 7. The generating unit 11 acquires an ultrasonic diagnostic image at the angle A of the ultrasonic wave emitting surface 4a for the ultrasonic waves 4, and redraws the ultrasonic diagnostic image on the image display 14.

As a result, the region which is important in diagnosing the specimen and which requires another observation is regenerated on the image display 14. Thus, it is possible to diagnose the ultrasonic diagnostic image at a desired angle, for example, at the angle A of the ultrasonic wave emitting surface 4a for the ultrasonic waves 4.

In this manner, according to the first embodiment described above, when the angle of the direction of the emitting surface for the ultrasonic waves 4 at which the ultrasonic cross-sectional image is generated is maintained for a given time, the angle information is saved in the angle information memory 8. Thus, it is possible to redraw the ultrasonic diagnostic image at the desired angle of the ultrasonic wave emitting surface 4a for the ultrasonic waves 4 with a simple operation and to achieve a reduction in diagnostic time.

For example, in the diagnosis using the transesophageal ultrasonic diagnostic apparatus, the ultrasonic wave emitting surface 4a is rotated on the axis in the direction of the arrow $R_1$ as shown in FIG. 2 during the diagnosis of the specimen, and a plurality of ultrasonic diagnostic images are sequentially generated on the image display 14 from a plurality of angular directions to a certain region within the specimen. During such an inspection of a certain region of the specimen, the angle of the ultrasonic wave emitting surface 4a remains unchanged for a preset given time in the diagnosis of the region which is important in diagnosing the specimen. This ensures that the angle information for the ultrasonic diagnostic image of the region which is important in diagnosing the specimen can be saved in the angle information memory 8.

Therefore, when the ultrasonic diagnostic image of the region which is important in diagnosing the specimen is regenerated from a desired angle, it is possible to redraw, on the image display 14, the ultrasonic diagnostic image of the region which is important in diagnosing the specimen with a simple operation; for example, operating the switch 5a for redrawing or touching the touch buttons 18a to 18d on the display screen 17 of the operation panel 15. As a result, it is possible to again diagnose the ultrasonic diagnostic image at the angle which is important in diagnosing the specimen.

The ultrasonic diagnostic image at a desired angle can be regenerated with a simple operation to achieve a reduction in inspection time, such that a certain region of the specimen can be diagnosed in real time owing to the regenerated ultrasonic diagnostic image at the desired angle. For example, when a region of the specimen is treated, for example, burned off, it is possible to administer a proper treatment by observing the regenerated ultrasonic diagnostic image in real time. Moreover, it is possible to redraw and observe in real time the ultrasonic diagnostic image of the region of the specimen after the treatment such as the burn-off has been administered.

In addition, the first embodiment described above may be modified in the following manner.

The regenerating unit 12 redraws the ultrasonic diagnostic image at one angle before the angle of the currently generated ultrasonic diagnostic image in accordance with the operation of the switch 5a for redrawing. This is not a limitation. For example, when the switch 5a for redrawing is operated N (=integer number) times in a row, the regenerating unit 12 may redraw the ultrasonic diagnostic image at the angle N times before the angle of the currently generated ultrasonic diagnostic image. In this case, the angle information N times before back in time is read out of the angle information saved in the angle information memory 8 in a time-series manner, and the ultrasonic cross-sectional image for the read angle information is regenerated.

Next, a second embodiment of the present invention will be described with reference to the drawing. It is to be noted that the same signs are assigned to the same parts as those in FIGS. 1 to 3, and these parts will not be described in detail.

When a predetermined condition is satisfied, for example, when the ultrasonic cross-sectional image generated on the image display 14 is saved in the image memory 10, the regenerating unit 12 saves the angle information for the saved ultrasonic cross-sectional image in the angle information memory 8.

The program for the ultrasonic diagnostic processing stored in the program memory 9 includes a program which causes the information on the angle of the ultrasonic wave emitting surface 4a for the ultrasonic waves 4 at which the saved ultrasonic cross-sectional image is generated to be saved in the angle information memory 8 when the ultrasonic cross-sectional image generated on the image display 14 is saved in the image memory 10

In such a configuration, the ultrasonic wave emitting surface 4a is rotated on the axis x in the direction of the arrow $R_1$ as shown in FIG. 2 during the diagnosis of the specimen in the same manner as described above. During the rotation of the ultrasonic wave emitting surface 4a, a plurality of ultrasonic diagnostic images are sequentially generated on the image display 14 from a plurality of angular directions to a certain region within the specimen.

During this diagnosis, if the ultrasonic diagnostic image at the angle which is important in diagnosing the specimen is generated on the image display 14 among the ultrasonic diagnostic images at the respective angles to the specimen, an operation is performed on the operation panel 15 for a save instruction. In response to the save instruction from the operation panel 15, the main control unit 6 saves the ultrasonic diagnostic image at the angle which is important in diagnosing the specimen in the image memory 10.

Figure 6:
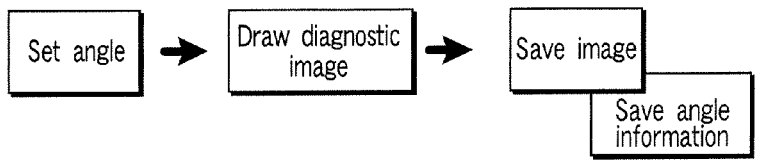
FIG. 6 is a diagram showing the flow of a method of saving the angle information for the ultrasonic diagnostic image in a second embodiment of the ultrasonic diagnostic apparatus according to the present invention.

At this point, the regenerating unit 12 saves, in the angle information memory 8, the information on the angle of the ultrasonic wave emitting surface 4a for the ultrasonic waves 4 at which the ultrasonic cross-sectional image saved in the image memory 10 is generated, as shown in FIG. 6. In addition, when there are a plurality of ultrasonic cross-sectional images saved in the image memory 10, the regenerating unit 12 sequentially saves, in the angle information memory 8, the information on the angle of the ultrasonic wave emitting surface 4a for the ultrasonic waves 4 at which each ultrasonic cross-sectional image is generated every time each ultrasonic cross-sectional image is saved in the image memory 10.

Along with this, the angle information display unit 13 displays a plurality of pieces of angle information saved in the angle information memory 8, for example, by indicating the touch buttons 18a to 18d for the four angles A to D as the angle information 18 on the display screen 17 of the operation panel 15 as shown in FIG. 4.

Next, in the case of redrawing the ultrasonic diagnostic image generated at the angle to the region which is important in diagnosing the specimen and which requires another observation, for example, at one angle before that of the ultrasonic diagnostic image currently generated on the image display 14, the switch 5a for redrawing provided in the operation portion 5 is operated, as in the first embodiment described above.

On the other hand, in the case of again diagnosing the ultrasonic diagnostic image of the region corresponding to the angle information 18 for the angle to the region which is important in diagnosing the specimen and which requires another observation, for example, the angle A displayed on the display screen 17 of the operation panel 15, the touch button 18a for the angle A is touched out of the angle information 18 displayed on the display screen 17 of the operation panel 15, as in the first embodiment described above. As a result of this operation, the ultrasonic diagnostic image at a desired angle to the region which is important in diagnosing the specimen, for example, at the angle A of the ultrasonic wave emitting surface 4a for the ultrasonic waves 4 is regenerated. Consequently, it is possible to again diagnose the ultrasonic diagnostic images at the angle A which is important in diagnosing the specimen.

In this manner, according to the second embodiment, when the ultrasonic cross-sectional image generated on the image display 14 is saved in the image memory 10, the information on the angle of the ultrasonic wave emitting surface 4a for the ultrasonic waves 4 at which this ultrasonic cross-sectional image is generated is saved in the angle information memory 8. Thus, the second embodiment can provide effects similar to those in the first embodiment described above.

Next, a third embodiment of the present invention will be described with reference to the drawing. It is to be noted that the same signs are assigned to the same parts as those in FIGS. 1 to 3, and these parts will not be described in detail.

When a predetermined condition is satisfied, for example, when the angle of the ultrasonic wave emitting surface 4a at which the ultrasonic cross-sectional image is generated on the image display 14 is changed, the regenerating unit 12 saves, in the angle information memory 8, the angle information indicating the angle of the ultrasonic wave emitting surface 4a at which the ultrasonic cross-sectional image is generated before the change of the angle of the ultrasonic wave emitting surface 4a.

The program for the ultrasonic diagnostic processing stored in the program memory 9 includes a program which causes the angle information indicating the angle of the ultrasonic wave emitting surface 4a at which the ultrasonic cross-sectional image is generated before the change of the angle of the ultrasonic wave emitting surface 4a to be saved in the angle information memory 8 when the angle of the ultrasonic wave emitting surface 4a at which the ultrasonic cross-sectional image is generated on the image display 14 is changed.

In such a configuration, the ultrasonic wave emitting surface 4a is rotated on the axis x in the direction of the arrow $R_1$ as shown in FIG. 2 during the inspection of the specimen in the same manner as described above, and a plurality of ultrasonic diagnostic images are sequentially generated on the image display 14 from a plurality of angular directions to a certain region within the specimen.

Figure 7:
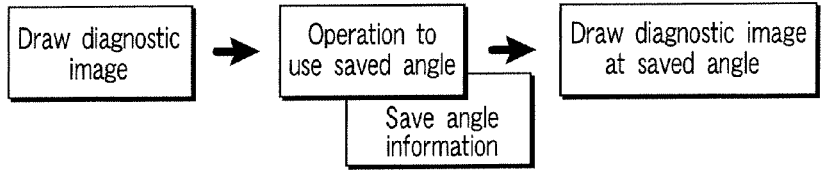
FIG. 7 is a diagram showing the flow of a method of saving the angle information for the ultrasonic diagnostic image in a third embodiment of the ultrasonic diagnostic apparatus according to the present invention.

During this diagnosis, when the angle for the ultrasonic diagnostic image is changed, the regenerating unit 12 saves, in the angle information memory 8, the angle information for the ultrasonic cross-sectional image generated before the change of the angle, as shown in FIG. 7. In addition, if the angle of the ultrasonic wave emitting surface 4a at which the ultrasonic diagnostic image is generated is changed a plurality of times, the regenerating unit 12 sequentially saves, in the angle information memory 8, the information on the angle of the ultrasonic wave emitting surface 4a at which the ultrasonic diagnostic image is generated, every time the angle is changed.

Along with this, the angle information display unit 13 displays a plurality of pieces of angle information saved in the angle information memory 8, for example, by indicating the touch buttons 18a to 18d for the four angles A to D as the angle information 18 on the display screen 17 of the operation panel 15 as shown in FIG. 4.

Next, in the case of redrawing the ultrasonic diagnostic image generated at the angle to the region which is important in diagnosing the specimen and which requires another observation, for example, at one angle before that of the ultrasonic diagnostic image currently generated on the image display 14, the switch 5a for redrawing provided in the operation portion 5 is operated, as in the first embodiment described above.

On the other hand, in the case of again diagnosing the ultrasonic diagnostic image of the region corresponding to the angle information 18 for the angle to the region which is important in diagnosing the specimen and which requires another observation, for example, the angle A displayed on the display screen 17 of the operation panel 15, the touch button 18a for the angle A is touched out of the angle information 18 displayed on the display screen 17 of the operation panel 15, as in the first embodiment described above.

As a result of this operation, the ultrasonic diagnostic image at a desired angle to the region which is important in diagnosing the specimen is regenerated. It is possible to again diagnose the ultrasonic diagnostic images at the angle which is important in diagnosing the specimen.

In this manner, according to the third embodiment, when the angle of the ultrasonic wave emitting surface 4a at which the ultrasonic cross-sectional image is generated on the image display 14 is changed, the angle information indicating the angle of the ultrasonic wave emitting surface 4a at which the ultrasonic diagnostic image is generated before the angle of the ultrasonic wave emitting surface 4a is changed is saved in the angle information memory 8. Thus, the third embodiment can provide effects similar to those in the first embodiment described above.

It is to be noted that the present invention is not limited to the embodiments described above, and may be modified in the following manner.

Figures 8A, 8B:
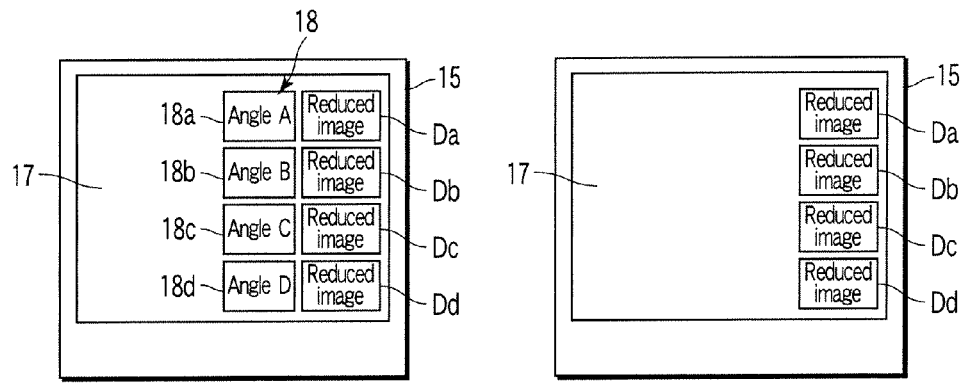
FIG. 8A is a diagram showing touch buttons and reduced ultrasonic cross-sectional images displayed on the display screen of the operation panel in the ultrasonic diagnostic apparatus according to the present invention.
FIG. 8B is a diagram showing the reduced ultrasonic cross-sectional images doubling as the touch buttons displayed on the display screen of the operation panel in the ultrasonic diagnostic apparatus according to the present invention.

For example, the angle information display unit 13 displays the touch buttons 18a to 18d for the four angles A to D as the angle information 18 on the display screen 17 of the operation panel 15 as shown in FIG. 4. This is not a limitation. For example, the angle information display unit 13 may display reduced ultrasonic cross-sectional images (thumbnail images) Da to Dd corresponding to the four angles A to D as well as the touch buttons 18a to 18d on the display screen 17 of the operation panel 15 as shown in FIG. 8A. The reduced images Da to Dd are displayed side by side with the touch buttons 18a to 18d, respectively.

The angle information display unit 13 may also display the reduced ultrasonic cross-sectional images (thumbnail images) Da to Dd corresponding to the four angles A to D alone on the display screen 17 of the operation panel 15 as shown in FIG. 8B. Each of the reduced images (thumbnail images) Da to Dd functions as a touch button. For example, when the reduced image Da is touched, the regenerating unit 12 redraws the ultrasonic diagnostic image at the angle A of the ultrasonic wave emitting surface 4a for the ultrasonic waves 4 on the image display 14.

The angle information display unit 13 displays a plurality of pieces of angle information saved in the angle information memory 8, for example, by indicating the touch buttons 18a to 18d for the four angles A to D as the angle information 18 on the display screen 17 of the operation panel 15 as shown in FIG. 4 and FIG. 8A. This is not a limitation, and the angle information display unit 13 may display the touch buttons 18a to 18d for the four angles A to D as the angle information 18 on the image display 14. The image display 14 displays, for example, an angle for the diagnosis of the specimen and a rotation angle of the transesophageal probe, and may display the angle information 18 together.

Figure 9:
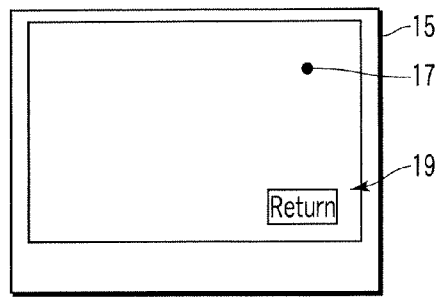
FIG. 9 is a diagram showing a return touch button displayed on the display screen of the operation panel in the ultrasonic diagnostic apparatus according to the present invention.
Figure 10:
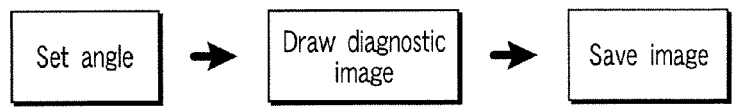
FIG. 10 is a diagram showing the flow of a conventional operation method of generating an ultrasonic diagnostic image.

For example, a return touch button 19 may be displayed on the display screen 17 of the operation panel 15 as shown in FIG. 9. The return touch button 19 sends, to the regenerating unit 12, a command to sequentially return to the previous drawing of the ultrasonic cross-sectional image at each operation. For example, the angle information for the four angles A to D is sequentially saved in the angle information memory 8. In this case, when the return touch button 19 is operated, the regenerating unit 12 draws the previous angle information from the angle information memory 8 in response to each operation of the return touch button 19. For example, if the ultrasonic diagnostic image at the angle D is generated at present, the regenerating unit 12 then draws the ultrasonic diagnostic image at the angle C. If the return touch button 19 is continuously operated, the regenerating unit 12 draws, for example, the ultrasonic diagnostic image at the angle D, then draws the ultrasonic diagnostic image at the angle C, then draws the ultrasonic diagnostic image at the angle B, and then draws the ultrasonic diagnostic image at the angle A.

A return switch is not limited to the return touch button 19 displayed on the display screen 17. The return switch may be provided on a surface other than the display screen 17 in the operation panel 15. For example, as shown in FIG. 1, a return switch 20 may be provided on a main unit front surface 21 of the ultrasonic diagnostic apparatus 1. The return switch 20 is, for example, a mechanical switch such as a push button or switch button, or a touch button exclusive to the return switch.

For example, when one return switch 20 is provided, return angle information allocated to the return switch 20 is displayed on, for example, the display screen 17 in the operation panel 15. If the return switch 20 is operated, the regenerating unit 12 redraws a particular ultrasonic cross-sectional image generated one image before.

When a plurality of mechanical return switches 20 such as the push buttons or switch buttons are provided on the main unit front surface 21 of the ultrasonic diagnostic apparatus 1, return angle information allocated to each of the return switches 20 is displayed on, for example, the display screen 17 in the operation panel 15. The return angle information includes, for example, the four angles A to D of the ultrasonic wave emitting surface 4a for the ultrasonic waves 4.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:
   an ultrasonic probe in which a surface emits ultrasonic waves and rotates the ultrasonic wave emitting surface centering on an axis included in the ultrasonic wave emitting surface;
   a generating unit configured to generate a plurality of ultrasonic cross-sectional images at a plurality of rotation angles when the ultrasonic wave emitting surface in the ultrasonic probe is rotated;
   an image display;
   an angle information memory; and
   a regenerating unit configured to
      save, to the angle information memory, information on a rotation angle when generating a first ultrasonic cross-sectional image in response to a condition being satisfied,
      regenerate the first ultrasonic cross-sectional image at the rotation angle by rotating the ultrasonic wave emitting surface of the ultrasonic probe based on the information of the rotation angle stored in the angle information memory when an instruction to regenerate the first ultrasonic cross-sectional image is received at a state of generating an ultrasonic cross-sectional image at an angle different from the rotation angle information saved on the angle information memory, and
      regenerate the first ultrasonic cross-sectional image on the image display,
   wherein the condition corresponds to a rotation angle of the ultrasonic wave emitting surface being maintained for a predetermined period of time or the rotation angle of the first ultrasonic cross-sectional image being changed.

2. An ultrasonic diagnostic apparatus comprising:
   an ultrasonic probe in which a surface emits ultrasonic waves and in which a plurality of ultrasonic wave oscillating elements are one-dimensionally arranged;
   an acoustic lens which converges ultrasonic waves emitted from the ultrasonic probe;
   a generating unit configured to mechanically rotate the ultrasonic probe with respect to the acoustic lens and configured to rotate the surface emitting the ultrasonic waves centering on an axis included in the surface emitting the ultrasonic waves to generate a three-dimensional ultrasonic cross-sectional image;
   an image display;
   an angle information memory; and
   a regenerating unit configured to save, to the angle information memory, information on a rotation angle when generating a first ultrasonic cross-sectional image in response to a condition being satisfied, regenerate the first ultrasonic cross-sectional image at the rotation angle by rotating the ultrasonic wave emitting surface of the ultrasonic probe based on the information of the rotation angle stored in the angle information memory when an instruction to regenerate the first ultrasonic cross-sectional image is received at a state of generating an ultrasonic cross-sectional image at an angle different from the rotation angle information saved on the angle information memory, and regenerate the first ultrasonic cross-sectional image on the image display, wherein the condition corresponds to a rotation angle of the ultrasonic wave emitting surface being maintained for a predetermined period of time or the rotation angle of the first ultrasonic cross-sectional image being changed.

3. An ultrasonic diagnostic apparatus comprising:

an ultrasonic probe in which a surface emits ultrasonic waves and in which a plurality of ultrasonic wave oscillating elements are two-dimensionally arranged;

a generating unit configured to control the operation of the ultrasonic probe to rotate the direction of the ultrasonic wave emitting surface centering on an axis included in the ultrasonic wave emitting surface and configured to generate a three-dimensional ultrasonic cross-sectional image; and a regenerating unit configured to save, to an angle information memory, information on a rotation angle when generating a first ultrasonic cross-sectional image in response to a condition being satisfied, regenerate the first ultrasonic cross-sectional image at the rotation angle by rotating the ultrasonic wave emitting surface of the ultrasonic probe based on the information of the rotation angle stored in the angle information memory when an instruction to regenerate the first ultrasonic cross-sectional image is received at a state of generating an ultrasonic cross-sectional image at an angle different from the rotation angle information saved on the angle information memory, and regenerate the first ultrasonic cross-sectional image on an image display;

wherein the condition corresponds to a rotation angle of the ultrasonic wave emitting surface being maintained for a predetermined period of time or the rotation angle of the first ultrasonic cross-sectional image being changed.

4. The ultrasonic diagnostic apparatus according to claim 1, 2 or 3, further comprising:

an operation unit configured to operate the ultrasonic probe; and a switch provided in the operation unit, wherein the regenerating unit is configured to rotate the ultrasonic wave emitting surface to the angle based on the saved rotation angle information when the switch is operated.

5. The ultrasonic diagnostic apparatus according to claim 1, 2 or 3, wherein the regenerating unit is configured to display, on the display screen of the operation panel, a return switch which instructs to return to a previous angle information, and regenerate a previously generated particular ultrasonic cross-sectional image when the return switch is operated.

6. The ultrasonic diagnostic apparatus according to claim 5, wherein the regenerating unit is configured to sequentially regenerate the ultrasonic cross-sectional image corresponding to the previous angle information every time the return switch is operated.

7. The ultrasonic diagnostic apparatus according to claim 1, 2 or 3, further comprising:

a return switch provided on a surface other than a display screen in an operation panel and configured to instruct to return to a previous angle information, wherein the regenerating unit is configured to regenerate an ultrasonic cross-sectional image corresponding to the previous angle information when the return switch is operated.

8. The ultrasonic diagnostic apparatus according to claim 7, wherein the regenerating unit is configured to sequentially regenerate the ultrasonic cross-sectional image corresponding to the previous angle information every time the return switch is operated.

9. The ultrasonic diagnostic apparatus according to claim 1, 2, or 3, further comprising:

an operation panel having a display screen; and an angle information display unit configured to display the rotation angle information stored on the angle information memory on the display screen of the operation panel, wherein the regenerating unit is configured to select the rotation angle information displayed on the display screen and rotate the ultrasonic wave emitting surface of the ultrasonic probe to the rotation angle based on the selected rotation angle.

10. The ultrasonic diagnostic apparatus according to claim 9, wherein the angle information display unit is configured to display, on the display screen, the rotation angle information and a reduced image of the first ultrasonic cross-sectional image corresponding to the rotation angle information.

11. The ultrasonic diagnostic apparatus according to claim 9, wherein the angle information display unit is configured to display in a first column, on the display screen, a plurality of rotation angle information, each of the plurality of rotation angle information being displayed alongside a corresponding reduced image corresponding to the respective rotation angle information, and the corresponding reduced images are displayed in a second column that is adjacent to the first column.

12. The ultrasonic diagnostic apparatus according to claim 1, wherein the condition corresponds to the rotation angle of the ultrasonic wave emitting surface being maintained for the predetermined period of time.

13. The ultrasonic diagnostic apparatus according to claim 1, wherein the condition corresponds to the rotation angle of the first ultrasonic cross-sectional image being changed.

14. An ultrasonic diagnostic processing method comprising:

rotating a surface emitting ultrasonic waves emitted from an ultrasonic probe centering on an axis included in the ultrasonic wave emitting surface;

generating a plurality of ultrasonic cross-sectional images at a plurality of rotation angles when the ultrasonic wave emitting surface in the ultrasonic probe is rotated;

saving, to an angle information memory, information on a rotation angle when generating a first ultrasonic cross-sectional image in response to a condition being satisfied; and regenerating the first ultrasonic cross-sectional image at the rotation angle by rotating the ultrasonic wave emitting surface of the ultrasonic probe in accordance with the rotation angle information saved on the angle information memory when receiving instruction to regenerate the first ultrasonic cross-sectional image at a state of generating an ultrasonic cross-sectional image at a rotation angle different from the rotation angle information saved on the angle information memory, and regenerating the first ultrasonic cross-sectional image on an image display, wherein the condition corresponds to a rotation angle of the ultrasonic wave emitting surface being maintained for a predetermined period of time or the rotation angle of the first ultrasonic cross-sectional image being changed.

15. An ultrasonic diagnostic processing method comprising:

mechanically rotating, with respect to an acoustic lens, an ultrasonic probe in which a plurality of ultrasonic wave oscillating elements are one-dimensionally arranged, and rotating a surface emitting ultrasonic waves emitted from the ultrasonic probe centering on an axis included in the ultrasonic wave emitting surface to generate a three-dimensional ultrasonic cross-sectional image on an image display;

saving, to an angle information memory, information on a rotation angle when generating a first ultrasonic cross-sectional image in response to a condition being satisfied;

regenerating the first ultrasonic cross-sectional image at the rotation angle by rotating the ultrasonic wave emitting surface of the ultrasonic probe in accordance with the rotation angle information saved on the angle information memory when receiving instruction to regenerate the first ultrasonic cross-sectional image at a state of generating an ultrasonic cross-sectional image at a rotation angle different from the rotation angle information saved on the angle information memory, and regenerating the first ultrasonic cross-sectional image on the image display, wherein the condition corresponds to a rotation angle of the ultrasonic wave emitting surface being maintained for a predetermined period of time or the rotation angle of the first ultrasonic cross-sectional image being changed.

16. An ultrasonic diagnostic processing method comprising:

controlling the operation of an ultrasonic probe in which a plurality of ultrasonic wave oscillating elements are two-dimensionally arranged, and rotating a surface emitting ultrasonic waves emitted from the ultrasonic probe centering on an axis included in the ultrasonic wave emitting surface to generate a three-dimensional ultrasonic cross-sectional image;

saving, to an angle information memory, information on a rotation angle when generating a first ultrasonic cross-sectional image in response to a condition being satisfied; and generating the first ultrasonic cross-sectional image at the rotation angle by rotating the ultrasonic wave emitting surface of the ultrasonic probe in accordance with the rotation angle information saved on the angle information memory when receiving instruction to regenerate the first ultrasonic cross-sectional image at a state of generating an ultrasonic cross-sectional image at a rotation angle different from the rotation angle information saved on the angle information memory, and regenerating the first ultrasonic cross-sectional image on an image display, wherein the condition corresponds to a rotation angle of the ultrasonic wave emitting surface being maintained for a predetermined period of time or the rotation angle of the first ultrasonic cross-sectional image being changed.

\* \* \* \* \*